United States Patent

Richard et al.

[11] Patent Number: 5,944,674
[45] Date of Patent: Aug. 31, 1999

[54] CONTROLLED TACK POLYURETHANE CASTING TAPE

[75] Inventors: Robert E. Richard, Rehoboth, Mass.; Richard Green, Livingston, N.J.; Ranga Ranganathan, Grand Rapids, Mich.

[73] Assignee: Johnson & Johnson Professional, Inc., Raynham, Mass.

[21] Appl. No.: 08/963,410

[22] Filed: Nov. 3, 1997

[51] Int. Cl.⁶ ........................................ A61F 5/00
[52] U.S. Cl. .................. 602/6; 252/135; 424/57
[58] Field of Search ................ 602/8; 252/135; 424/57, 58

[56] References Cited

U.S. PATENT DOCUMENTS 5,342,535   8/1994   Ramirez et al. ................... 252/135

*Primary Examiner*—Jerome W. Donnelly
*Assistant Examiner*—Kelvin Hart
*Attorney, Agent, or Firm*—Joseph F. Shirtz

[57] ABSTRACT

A polyurethane casting tape with controlled tack is disclosed. The tackiness of the polyurethane is controlled by the addition of combinations of Kurrol salts, potassium metaphosphate and a sodium salt.

6 Claims, No Drawings

CONTROLLED TACK POLYURETHANE CASTING TAPE

FIELD OF THE INVENTION

The present invention relates to an improved orthopedic casting tape. The casting tapes of the present invention provide improved workability and moldability which allows better application of the casting tapes to the patient and the resulting cast better fits and conforms to the patient's limb. The use of the tack control agents in the casting tapes of the present invention also provides improvements in the physical properties of casts made with the casting tapes.

BACKGROUND OF THE INVENTION

Plaster of Paris casts have been in use to immobilize body members or limbs for some time. The plaster of Paris bandages have been supplemented and, to some extent, superseded by synthetic cast tapes or bandages which employ polymeric materials on a substrate. The preferred polymeric materials are water-cured or water-reactive polyurethane compositions. The polyurethane materials have largely supplanted other polymeric synthetic casting materials. These polyurethane casting materials are of the type which are disclosed in U.S. Pat. No. 4,376,438, U.S. Pat. No. 4,411,262, and U.S. Pat. No. 4,433,680.

The fibrous substrate used in the synthetic casting materials is usually a polyester or fiberglass. Although knitted substrates are most common, woven substrates have also been used. The fiberglass materials offer advantages in terms of strength of the finished cast and various constructions of fiberglass fabrics have been used for the substrates for the synthetic casting tapes. U.S. Pat. Nos. 3,686,725, 3,787,272 and 3,882,857 disclose specific fiberglass materials, or the treatment of fiberglass yarns, to produce fiberglass substrates which are particularly suitable for use in orthopedic casts.

U.S. Pat. No. 4,323,061 discloses a cast substrate made from a combination of glass fibers and a second fiber such as cotton, flax, rayon, wool, acrylic resin, nylon, Teflon or polyester. The purpose of the second fiber in the substrate is to hold the curable resin on the substrate.

Casting tapes with improved conformability combine extensible and nonextensible yarns in the tape substrate are disclosed in U.S. Pat. Nos. 4,668,563; 4,940,047; 5,027,804; 5,256,134; 5,382,466; and 5,403,267.

U.S. Pat. Nos. 4,667,661 and 4,774,937 and 4,937,146 disclose the use of various lubricious materials as additives to the water hardenable materials used in casting tapes to reduce the tackiness of the water hardenable polyurethane resins and allow easier molding of the casting tape to the limbs of the patient. Also disclosed is the modification of the water hardenable prepolymer itself to provide lubricating effects. These lubricious materials interfere to some extent with the lamination of the successive layers of the casting tape to one another when the cast is applied to the patient. Inadequate lamination can result in finished casts with less than the desired strength characteristics.

U.S. Pat. Nos. 5,061,555 and 5,180,632 disclose casting tapes in which the prepolymer contains a hydrophilic bisureathane as a detackifying agent.

SUMMARY OF THE INVENTION

The present invention provides a casting tape with controlled tack, that is, reduced tack along the length of the cast or tangentially to the applied casting tape but normal high tack perpendicular to the applied casting tape. The reduction in the tangential tack allows for easier molding of the casting tape to the limb of the patient cast but does not significantly interfere with the tackiness or adherence of adjacent layers of the casting tape as the casting tape is applied to the patient.

The inorganic salts that have been found useful in the present tack reducing application are combinations of alkali metal Kurrol salts and sodium salts. Typical of the alkali metal Kurrol salts is potassium metaphosphate and typical of the sodium salts is sodium chloride.

DETAILED DESCRIPTION OF THE INVENTION

The substrate of the casting tape of the present invention is constructed i.e. woven or knitted, with a combination of continuous filament high tenacity yarns such as fiberglass yarns or lower tenacity yarns such as polyester yarn or a combination of fiberglass and polyester yarns and extensible yarns such as those disclosed in the patents mentioned above. The polyurethane prepolymer may be any of the prepolymers commonly used for casting tapes, the prepolymer with the catalyst disclosed in U.S. Pat. No. 4,433,680 being particularly preferred.

The present invention relates to the use of alkali metal salt, of the type referred to as Kurrol's salts, to improve the application characteristics of a water reactive polyurethane based orthopedic casting tape. Kurrol's salts are metaphosphates which can have a high molecular weight or a ring structure and have the empirical formula $MPO_3$ where M is an alkali metal such as lithium, sodium, potassium, rubidium or cesium. Of these the potassium salt is preferred for this invention. The alkali metal Kurrol's salts are not generally soluble in water but can be made soluble by ion exchange using a different metal salt to supply a different cation. Sodium salts with high water solubility are the preferred solubilizing salts. Once soluble, these compounds have been found to produce an interface at the surface of a polyurethane prepolymer which facilitates the application of such casting tapes to the patient.

The process of solubilizing the Kurrol's salt can be carried out in a number of ways. A mixture of the Kurrol's salt and a second salt containing a different cation can be made and applied to the prepolymer or mixed with it or the secondary salt can be supplied at a later time, such as by introduction through the dipwater used to activate the casting tape. Alternately the second salt can be introduced to the Kurrol's salt containing prepolymer by other vehicles such as from a coating on a glove which are used to handle the casting tape during application to the patient.

The potassium salt that have been found to useful in the present invention is potassium metaphosphate The sodium salts found to be useful include sodium chloride, sodium bicarbonate, sodium carbonate, tribasic sodium phosphate, sodium polyphosphate and the sodium salt of poly(acrylic acid). Effervescing materials containing these sodium salts may also be used.

If the salts are combined and added to the prepolymer, they are generally used in amounts of from 1 to 99% of the sodium salt and 99 to 1% of the potassium salt. The combined salts may be added to the prepolyer before the prepolymer is coated on the substrate or may be added to the substrate at the same time as the prepolymer. The total amount of the combined salts added to the prepolymer is from about one percent to about five percent, by weight, based on the weight of the prepolymer. If one of the salts is added to the dip water, it is preferably the sodium salt that is added to the dipwater. It would be added to the dipwater in an amount of from 0.1 percent to 10 percent, by weight based on the weight of the dipwater.

The effect of the salts on the tangential lubricity of the casting tape can be tested using the test for the Kinetic Coefficient of Friction (KCOF) set forth in U.S. Pat. Nos. 4,667,661 and 4,774,937. As defined in those patents, the KCOF of the casting tapes should be less than 1.2 when measured 30 seconds after the immersion of the casting tape in dip water. Although the casting tapes of the present invention do not have these KCOF characteristics, they do have significantly reduced tangential tack and are much easier to mold than similar tapes not containing the salts.

In the following Examples, the $KPO_3$ (water insoluble) and the salt (water soluble) could be combined together and added to the resin at some point. When they are dipped in water the salt dissolves, interacts with the $KPO_3$ to give the non-tack properties. In the following examples, the KCOF measurements were made using the procedure disclosed in U.S. Pat. Nos. 4,667,661 and 4,774,937. The equipment used was either a Sintech MTS 2/G run at 40 in/min. or an Instron model 1122 (both with and without MTS Renew System) operated at 50 in/min.

The delamination strength measurements were conducted using the procedure disclosed in U.S. Pat. No. 5,273,802. The equipment used was an Instron model 1122 (with an MTS ReNew System) operated at 50 in/min.

The crush strength measurements were made using a Sintech MTS 2/G which was run at a deformation speed of 12 in/min. The 5 layer compression cylinders were prepared by immersing the casting tape bandage into water at 75± F., squeezing lightly 4 to 5 times under the surface of the water, then wrapping the required number of layers on a 2.75 inch mandrel. The cylinders are removed from the mandrel once set and tested at the specific time of interest. Each date point reported is an average of a minimum of 4 tests.

EXAMPLE 1

Coated 4 grams (about 5% by weight relative to the resin on the bandage) of a 50/50 mixture of $KPO_3$ and NaCl onto a premanufactured bandage. When the bandage was dipped in water and rolled, it was slippery when rubbed, but tacky when squeezed.

EXAMPLE 2

Coated 1 gram (about 1.25% by weight relative to the resin on the bandage) of a 50/50 mixture of $KPO_3$ and sodium polyphosphate onto a bandage. When the bandage was dipped in water and rolled it was slippery when rubbed, but tacky when squeezed.

EXAMPLE 3

For these experiments two systems were looked at consisting of KPO3 with sodium chloride or with sodium polyphosphate $(NaPO_3)_x$. In each case the $KPO_3$ was mixed with an equal weight of sodium compound and sprinkled onto precoated, at various levels on commercially available polyurethane casting tapes sold under the name DELTA-LITEX Conformable. The levels of additive we investigated correspond to about 2–6 weight % of the prepolymer. The bandages were then placed in new pouches and sealed. These bandages were tested for Kinetic Coefficient of Friction (KCOF). (The test was conducted on the Instron 1122, using Series IX software.) In addition, only the side of each bandage containing the additive was measured, and only in the line/no ravel direction. The KCOF was measured at various time intervals to see what changes could be observed. The data is shown in Table 1.

TABLE 1

KCOFs for DELTA-LITE ® Conformable bandages coated with KPO3 and either NaCl or $(NaPO_3)_x$

| Sodium Compound | Amount/roll (grams) | KCOF at: | | |
|---|---|---|---|---|
| | | 30 sec. | 1 min. | 2 min. |
| none, control | 0 | 1.88 | 2.25 | 0.76 |
| NaCl | 1.1 | 1.86 | 1.95 | 0.71 |
| NaCl | 1.7 | 1.07 | 1.78 | 0.69 |
| NaCl | 2.5 | 1.74 | 1.74 | 0.69 |
| NaCl | 4.2 | 1.85 | 1.38 | 0.47 |
| NaCl | 7.3 | 1.08 | 0.96 | 0.53 |
| $(NaPO3)x$ | 1.9 | 1.81 | 1.11 | 0.58 |
| $(NaPO3)x$ | 2.7 | 1.83 | 1.66 | 0.60 |
| $(NaPO3)x$ | 4.9 | 1.46 | 1.66 | 0.44 |
| $(NaPO3)x$ | 7.6 | 0.98 | 1.19 | 0.41 |

The data indicates that at low salt levels the KCOF does not change appreciably compared to the control with no salt. When these bandages were dipped in water and rolled, they were slippery when rubbed but tacky when squeezed.

In the following examples, the potassium metaphosphate was mixed with the prepolymer while the salt is introduced from the dipwater.

EXAMPLE 4

Premanufactured bandages were coated with 1–3 grams of the $KPO_3$ and resealed into foil pouches. The bandages were dipped in water containing various sodium salts and rolled. The results are shown below in Table 2. In all cases, the casting tape was slippery when laminated (rubbing) and tacky when molded (squeezed). When pure water was used as a control, the casting tape could not be laminated without experiencing unacceptable tackiness.

TABLE 2

Sodium Salts Used in Dip Water

| Sodium Compound | Conc. in Dip Water |
|---|---|
| Sodium Chloride | 2% (20 grams in 1 liter water) |
| Trisodium Citrate | 2% |
| Sodium Bicarbonate | 1% |
| Sodium Carbonate | 2% |
| Trisodium Phosphate | 0.8% |
| Sodium Polyphosphate | 2% |
| Poly(sodium acrylate) | 1.5% |

EXAMPLE 5

Potassium metaphosphate ($KPO_3$) was mixed with sodium polyphosphate (NaPO3)s in different weight ratios from 10 to 50 parts of the potassium metaphosphate in 100 parts of the mixture. The mixture was distributed on the surface of the polyurethane casting tape made in accordance with the examples of U.S. Pat. No. 4,433,680. The amount of the mixture adding to the surface of the casting tape was varied between 0.52 grams and 4.5 grams. The KCOF of the surface of the tape to which the salt mixture was affixed was determined by the procedure set forth in U.S. Pat. No. 4,667,661. The KCOF test was run at times of 30, 60 and 120 seconds after the casting tape was immersed in the dipwater. The results are shown in Table 3.

TABLE 3

KCOF Measurements for Casting Tapes Containing Various Ratios of KPO3 and (NaPO3)x Amount in grams

Mixture 1 50K/50Na

| Time/KCOF | 0 | 1.1 | 1.9 | 2.9 | 3.3 | 4.5 |
|---|---|---|---|---|---|---|
| 30 | 1.83 | 1.41 | 1.72 | 1.43 | 1.59 | 1.7 |
| 60 | 2.1 | 1.34 | 1.89 | 1.61 | 1.74 | 1.78 |
| 120 | 2.1 | 0.39 | 1.16 | 0.53 | 0.91 | 1.46 |

Mixture 2 40K/60Na

| Time/KCOF | 0 | 1 | 1.55 | 2 | 2.8 | 3.25 |
|---|---|---|---|---|---|---|
| 30 | 1.83 | 1.85 | 1.82 | 1.74 | 1.67 | 1.74 |
| 60 | 2.1 | 1.8 | 1.8 | 1.83 | 1.9 | 1.8 |
| 120 | 2.1 | 1.73 | 0.95 | 0.76 | 0.54 | 1 |

Mixture 3 25K/75Na

| Time/KCOF | 0 | 1.1 | 1.9 | 2.9 | 3.6 |
|---|---|---|---|---|---|
| 30 | 1.83 | 1.76 | 1.92 | 1.82 | 1.65 |
| 60 | 2.1 | 1.86 | 1.91 | 1.75 | 1.39 |
| 120 | 2.1 | 1.65 | 0.56 | 0.39 | 0.37 |

Mixture 4 10K/90Na

| Time/KCO | 0 | 1 | 2 | 2.7 | 3.1 | 3.8 |
|---|---|---|---|---|---|---|
| 30 | 1.83 | 2.03 | 1.61 | 1.35 | 1.5 | 1.47 |
| 60 | 2.1 | 2.01 | 1.64 | 1.69 | 1.49 | 1.46 |
| 120 | 2.1 | 0.71 | 0.38 | 0.75 | 0.32 | 0.31 |

Mixture 6 30K/70Na

| Time/KCO | 0 | 1 | 2.1 | 3.2 | 3.7 | 4.2 |
|---|---|---|---|---|---|---|
| 30 | 1.83 | 1.6 | 1.48 | 1.36 | 1.38 | 1.62 |
| 60 | 2.1 | 1.23 | 1.56 | 1.37 | 0.88 | 1.15 |
| 120 | 2.1 | 0.5 | 0.61 | 0.49 | 0.41 | 0.33 |

EXAMPLE 6

Casting tape samples were prepared in a manner similar to those described in Example 5. The samples were then subjected to KCOF measurements using both 40 and 50 in/min. cross head speeds. The KCOF measurements were made at 30, 60 and 120 seconds from immersion of the tapes in water. The resulting data is shown in Table 4. The results showed that the KCOF at 50 in/min. are higher then those measured at 40 in/min., and that the KCOF's at 30 seconds were always greater than 1.2.

TABLE 4(a)

| Weight % of KPO3 and (NaPO3)x | 50K/50Na | | 40K/60Na | | 25K/75Na | |
|---|---|---|---|---|---|---|
| Additive Weight | 1.8 g | 1.9 g | 1.4 g | 1.4 g | 1.9 g | 1.95 g |
| Crosshead Speed (in/min.) | 40 | 50 | 40 | 50 | 40 | 50 |
| Time (seconds) | | | | | | |
| 30 | 1.48 | 1.74 | 1.57 | 1.57 | 1.62 | 1.77 |
| 60 | 1.61 | 1.88 | 1.96 | 1.87 | 1.78 | 1.64 |
| 120 | 1.37 | 1.12 | 0.45 | 0.84 | 0.49 | 0.53 |
| 30 | 1.50 | 1.68 | 1.38 | 1.59 | 1.44 | 1.46 |
| Additive Weight | 2.5 g | 2.7 g | 2.2 g | 2.1 g | 3.2 g | 3.4 g |
| Crosshead Speed (in/min.) | 40 | 50 | 40 | 50 | 40 | 50 |
| Time (seconds) | | | | | | |
| 30 | 1.76 | 1.48 | 1.58 | 1.64 | 1.55 | 1.59 |
| 60 | 1.78 | 1.62 | 1.17 | 1.56 | 1.51 | 0.90 |
| 120 | 0.39 | 0.91 | 0.39 | 0.96 | 0.41 | 0.27 |
| 30 | 1.42 | 1.74 | 1.24 | 1.37 | 1.30 | 1.06 |

Measurements taken at 40 in/min. were made on the Sintech MTS 2/G Test Machine

Measurements taken at 50 in/min. were made on the MTS ReNew System (formerly the Instron 1122)

TABLE 4(b)

| Weight % of KPO3 and (NaPO3)x | 10K/90Na | | 30K/70Na | | Control | |
|---|---|---|---|---|---|---|
| Additive Weight | 1.15 g | 1.1 g | 1.8 g | 1.8 g | 0 | 0 |
| Crosshead Speed (in/min.) | 40 | 50 | 40 | 50 | 40 | 50 |
| Time (seconds) | | | | | | |
| 30 | 1.37 | 1.79 | 1.43 | 1.57 | 1.44 | 1.80 |
| 60 | 1.79 | 1.43 | 1.80 | 1.51 | 1.67 | 1.89 |
| 120 | 0.4 | 0.78 | 1.01 | 0.87 | 1.11 | 1.53 |
| 30 | 1.52 | 1.55 | 1.40 | 1.28 | 1.62 | 1.64 |
| Additive Weight | 3.1 g | 3.1 g | 2.35 g | 3.3 g | | |
| Crosshead Speed (in/min.) | 40 | 50 | 40 | 50 | 40 | 50 |
| Time (seconds) | | | | | | |
| 30 | 1.76 | 1.59 | 1.52 | 1.36 | | |
| 60 | 1.65 | 1.33 | 1.58 | 1.55 | | |
| 120 | 0.38 | 0.74 | 0.33 | 0.45 | | |
| 30 | 1.11 | 1.57 | 1.46 | 1.35 | | |

Measurements taken at 40 in/min. were made on the Sintech MTS 2/G Test Machine

Measurements taken at 50 in/min. were made on the MTS ReNew System (formerly the Instron 1122)

EXAMPLE 7

Dry mixtures of KPO3 and (NaPO3)x were made by adding the salts to a plastic jar and then mixing on a roll mill for a minimum of 4 hours. Mixtures were made with the following compositions:

Mixture A: 40 weight % KPO3 and 60 weight % (NaPO3)x

Mixture B: 25 weight % KPO3 and 75 weight % (NaPO3)x

The mixtures were then coated onto premanufactured 3 inch wide casting tapes while in a controlled low humidity environment and then repackaged. KCOF measurements were taken at both 40 and 50 in/min. crosshead speeds. The KCOF measurements were made at 30, 60 and 120 seconds from immersion of the tapes in water. The resulting data is shown in Table 5. The results showed that the KCOF at 50 in/min. are generally higher then those measured at 40 in/min., and that the KCOF's at 30 seconds were always greater than 1.2.

TABLE 5

| Bandages I.D. | Mix A | | Mix B | |
|---|---|---|---|---|
| Additive Quantity (g) | 2.64 | 2.35 | 2.74 | 2.62 |
| Crosshead Speed | 40 in/min | 50 in/min | 40 in/min | 50 in/min |
| Time (seconds) | | | | |
| 30 | 1.47 | 1.45 | 1.09 | 1.41 |
| 60 | 1.50 | 1.25 | 1.04 | 1.62 |
| 120 | 0.35 | 0.36 | 0.24 | 1.13 |
| 30 | 1.13 | 1.23 | 1.07 | 1.48 |

Measurements taken at 40 in/min were made on the Sintech MTS 2/G Test Machine

TABLE 5-continued

| Bandages I.D. | Mix A | Mix B |
|---|---|---|

Measurements taken at 50 in/min were made on the MTS ReNew System (formerly the Instron 1122)

EXAMPLE 8

Three inch bandages containing either salt mixture A or B were prepared as described in Example 7. The bandages were then used to prepare 5 layer compression cylinders with an inside diameter of 2.75 inches in order to measure the crush strength of the resulting products. The amount of salt mixture added to each bandage was between 2 and 3 grams. As a control, bandages without the salt additives were also measured for crush strength. The results in Table 6 show the crush strength at 15 and 30 minutes as well as 24 hours along with the 24 hour weight of the test cylinders. The results indicate an increase in the crush strength compared to the control with no salt additives.

TABLE 6

| Strength | Mixture A | | Mixture B | | Control | | |
|---|---|---|---|---|---|---|---|
| 15 min (lb.) | 48.5 | 44.1 | 58.7 | 55.2 | 42.9 | 41.0 | 33.0 |
| 30 min (lb.) | 77.8 | 74.7 | 90.1 | 88.7 | 72.6 | 74.0 | 54.0 |
| 24 hrs (lb.) | 125.3 | 123.8 | 138.8 | 139.0 | 115.9 | 113.0 | 100.0 |
| 24 weight (g) | 56.3 | 57.5 | 56.9 | 57.6 | 54.1 | 52.0 | 51.0 |

EXAMPLE 9

Three inch bandages containing either salt mixture A or B were prepared as described in example 7. The bandages were then used to prepare 6 layer cylinders with an inside diameter of 2.0 inches in order to measure the delamination strength of the resulting products according to the procedure described in U.S. Pat. No. 5,273,802. The amount of salt mixture added to each bandage was between 2 and 3 grams. As a control, bandages without the salt additives or with a "tack-free lubricant" were also measured for delamination strength. The results in Table 7 show the delamination strength at 30 minutes. The results indicate an increase in the delamination strength for the casting tapes containing either the A or B salt mixture compared to the controls with no salt additives, or with the tack-free lubricant.

TABLE 7

| Sample | 30 min Delamination Strength (N/cm) |
|---|---|
| Control | 5.7 ± 0.3 |
| | 5.5 ± 0.4 |
| Competitive Product with tack-free lubricant | 4.4 ± 0.7 |
| | 2.2 ± 0.2 |
| Mixture A | 6.2 ± 0.2 |
| | 5.9 ± 1.4 |
| Mixture B | 6.9 ± 1.0 |
| | 6.7 ± 0.7 |

EXAMPLE 10

Three inch bandages containing either salt mixture A or B were prepared as described in example 7. The amount of salt mixture added to each bandage was between 2 and 3 grams. The bandages were incubated at 70° C. along with a control containing no salt additives. The elevated temperature was designed to simulate the accelerated aging of the polyurethane prepolymer by increasing the rate at which the reactions that lead to curing occurred. The bandages were then removed from the ovens at various intervals (3 bandages per interval) to determine their functionality as defined by the ability of samples to be unwound using minimal force. The test was carried out for a period of 14 days. The results of the test are shown in Table 8 and indicate that the presence of the salts did not change the aging properties of the prepolymer compared to the control suggesting that the shelf life is not affected by the addition of the salt additives.

TABLE 8 (a)

| Control | | | |
|---|---|---|---|
| | Sample | Results | Days |
| In | 15 | n/a | 0 |
| Out | 3 | OK | 4 |
| Out | 3 | OK | 7 |
| Out | 3 | OK | 8 |
| Out | 3 | OK* | 11 |
| Out | 3 | OK* | 14 |

OK* — Slightly difficult to unwind, the sample is functional

TABLE 8 (b)

| | Sample | Results | Days |
|---|---|---|---|
| | Mixture A | | |
| In | 15 | n/a | 0 |
| Out | 3 | OK | 4 |
| Out | 3 | OK | 7 |
| Out | 3 | OK | 8 |
| Out | 3 | OK* | 11 |
| Out | 3 | OK* | 14 |
| | Mixture B | | |
| In | 15 | n/a | 0 |
| Out | 3 | OK | 4 |
| Out | 3 | OK | 7 |
| Out | 3 | OK | 8 |
| Out | 3 | OK | 11 |
| Out | 3 | OK* | 14 |

OK* = Slightly difficult to unwind, the sample is functional

EXAMPLE 11

2000 grams of a 10% sodium bicarbonate solution was added to 3000 grams of a 56% natural rubber latex. Unexpectedly, the latex did not coagulate. This latex/bicarbonate overdip was used to coat natural rubber latex gloves by hand dipping on ceramic glove formers. These gloves were used to apply bandages coated with 1–3 grams of the KPO3 which had been resealed into foil pouches. In all cases, the casting tape was slippery when laminated (rubbing) and tacky when molded (squeezed).

What is claimed is:

1. An orthopedic casting tape comprising a flexible fabric substrate coated with a water reactive hardenable polyurethane prepolymer resin, said resin containing a potassium metaphosphate salt which will react with a sodium salt to produce a lubricious film on contact with water.

2. The orthopedic casting tape of claim 1 in which the sodium salt is selected from the group consisting of sodium chloride, sodium bicarbonate, sodium carbonate, tribasic sodium phosphate, sodium polyphosphate and sodium polyacrylate.

3. An orthopedic casting tape comprising a flexible fabric substrate coated with a water reactive hardenable polyurethane prepolymer resin, said resin containing a potassium metaphosphate salt and a sodium salt selected from the group consisting of sodium chloride, sodium bicarbonate, sodium carbonate, tribasic sodium phosphate and sodium polyphosphate.

4. The orthopedic casting tape of claim 3 in which the potassium metaphosphate and sodium salts are present in the prepolymer as a coating on the exposed surface of the casting tape.

5. The orthopedic casting tape of claim 4 in which the potassium metaphosphate and sodium salts are present in an amount of from 0.1 to 10% based on the weight of the prepolymer.

6. The orthopedic casting tape of claim 3 in which the weight ratio of the potassium metaphosphate salt to the sodium salt is between 0.01 to 1 and 1 to 1.

* * * * *